United States Patent

Tsao

[11] 4,042,640
[45] Aug. 16, 1977

[54] OXYCHLORINATION OF HYDROCARBONS

[75] Inventor: Utah Tsao, Jersey City, N.J.

[73] Assignee: The Lummus Company, Bloomfield, N.J.

[21] Appl. No.: 629,361

[22] Filed: Nov. 6, 1975

[51] Int. Cl.² .................................................. C07C 17/15
[52] U.S. Cl. ................................................... 260/659 A
[58] Field of Search ...................................... 260/659 A

[56] References Cited

U.S. PATENT DOCUMENTS

| 2,407,828 | 9/1946 | Gorin | 260/659 A |
|---|---|---|---|
| 3,055,955 | 9/1962 | Hodges | 260/659 A |
| 3,468,968 | 9/1969 | Baker et al. | 260/659 A |
| 3,551,506 | 12/1970 | Weinstein | 260/659 A |
| 3,557,229 | 1/1971 | Riegel | 260/659 A |
| 3,594,428 | 7/1971 | Antonini et al. | 260/659 A |
| 3,919,336 | 11/1975 | Kurtz | 260/659 A |
| 3,923,913 | 12/1975 | Antonini et al. | 260/659 A |
| 3,950,443 | 4/1976 | Prahl | 260/659 A |

Primary Examiner—Delbert E. Gantz
Assistant Examiner—J. Thierstein
Attorney, Agent, or Firm—Marn & Jangarathis

[57] ABSTRACT

In the oxychlorination of a hydrocarbon, the ratio of hydrocarbon feed to hydrogen chloride feed is maintained within set limits in response to changes in the concentration of aqueous hydrogen chloride recovered from the oxychlorination effluent. The concentration of aqueous hydrogen chloride recovered from the effluent may be determined either by conductivity and/or density.

7 Claims, 1 Drawing Figure

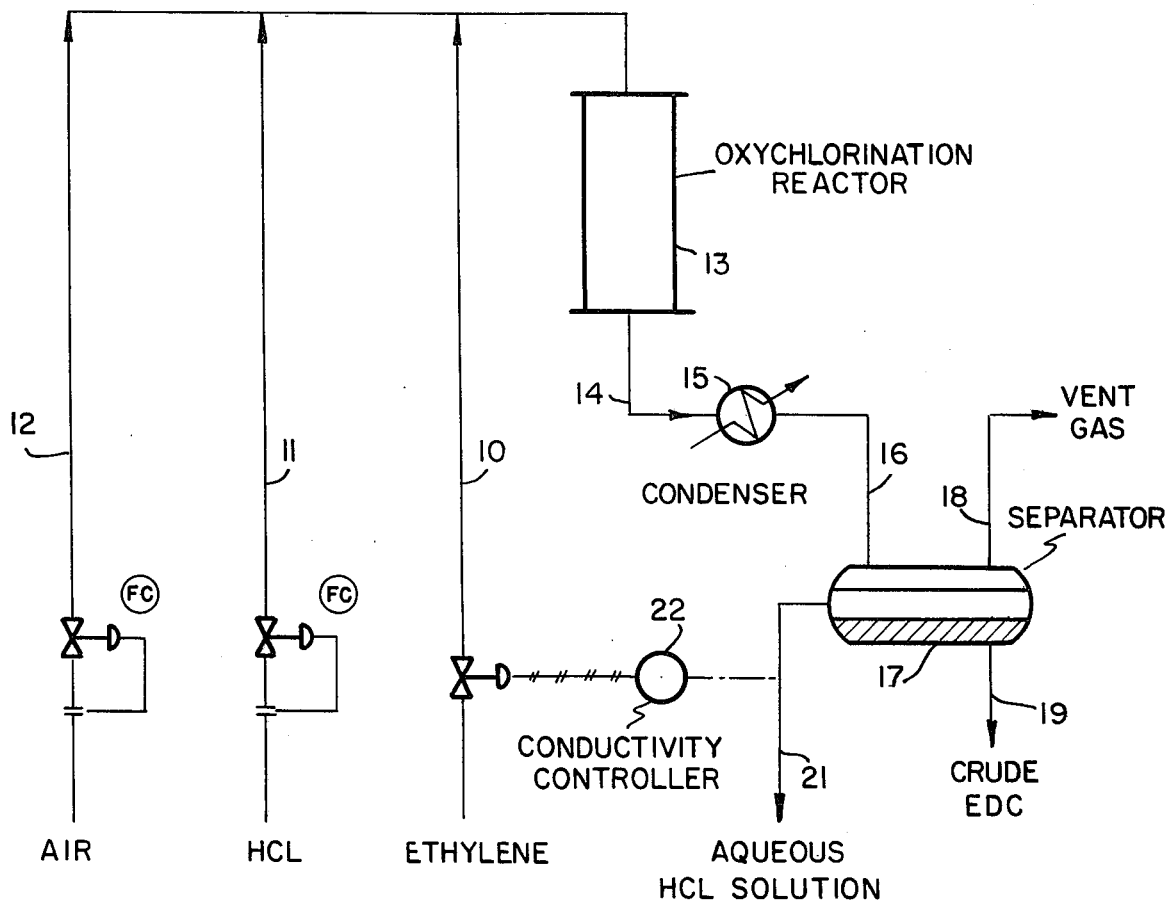

OXYCHLORINATION OF HYDROCARBONS

This invention relates to the production of chlorinated hydrocarbons, and more particularly to the oxychlorination of hydrocarbons to chlorinated hydrocarbons.

In the oxychlorination of hydrocarbons, in many cases, it is highly desirable to control the ratio of hydrogen chloride feed to hydrocarbon feed in order to optimize yield. Thus, for example, in the oxychlorination of ethylene, in many cases, the amounts of ethylene and hydrogen chloride introduced into the reactor should be maintained close to stoichiometric ratios in order to achieve optimum yields, in that any inbalance results in either loss of ethylene and/or hydrogen chloride in the vent stream. In most plants, the hydrogen chloride and ethylene feed are measured by gas flow meters and as a result, it is impractical to maintain the exact desired flow ratio by flow measurement.

An object of the present invention is to provide for production of chlorinated hydrocarbons by an oxychlorination process.

Another object of this invention is to provide for improved control of hydrogen chloride and/or hydrocarbon feed to an oxychlorination process.

Another object of the present invention is to control the ratio of hydrogen chloride to hydrocarbon feed in an oxychlorination process.

These and other objects of the present invention should be more readily apparent from reading the following description thereof.

In accordance with the present invention, a hydrocarbon is oxychlorinated by direct contact with oxygen and hydrogen chloride to produce an oxychlorination effluent containing chlorinated hydrocarbon, water vapor and hydrogen chloride. An aqueous hydrogen chloride solution is recovered from the effluent and the hydrogen chloride concentration thereof is determined, with the ratio of hydrogen chloride to hydrocarbon feed being decreased and increased in response to decreases and increases, respectively, in the hydrogen chloride concentration of the recovered aqueous hydrogen chloride solution to maintain a predetermined hydrogen chloride to hydrocarbon feed ratio.

More particularly, the amount of hydrogen chloride present in an oxychlorination effluent is determined by the relative proportions of hydrogen chloride and hydrocarbon in the feed to the oxychlorination reaction. Thus, for example, in the oxychlorination of ethylene, a 1% change in the hydrogen chloride to ethylene feed ratio at about stoichiometric ratios results in a 40% change in the hydrogen chloride concentration of the aqueous hydrogen chloride solution recovered from the effluent. As a result, the relative ratio of hydrogen chloride to hydrocarbon feed can be controlled in response to the hydrogen chloride concentration of an aqueous hydrogen chloride stream recovered from the oxychlorination reaction effluent.

The hydrogen chloride concentration of the aqueous hydrogen chloride solution recovered from the oxychlorination reaction effluent can be determined by any one of a wide variety of procedures, with such concentrations preferably being determined by either the conductivity of the hydrogen chloride solution or the density of the hydrogen chloride solution, with a conductivity determination being especially preferred. A conductivity determination is preferred in that the change in conductivity of the aqueous hydrogen chloride solution, at low hydrogen chloride concentrations, is more sensitive to hydrogen chloride concentration than density. Furthermore, conductivity meters are more accurate than density meters. The instrumentation employed for determining the conductivity and/or density of an aqueous hydrogen chloride solution are well known in the art, and no details with respect to such instrumentation and/or the manner in which such instrumentation can be employed to control the quantity of hydrogen chloride and/or hydrocarbon introduced into the oxychlorination reaction zone is deemed necessary for a complete understanding of the present invention.

The process for oxychlorinating hydrocarbons is well known in the art. In general, the hydrocarbon to be oxychlorinated is contacted with hydrogen chloride and molecular oxygen (the molecular oxygen is generally provided as air or oxygen enriched air) in the presence of an oxychlorination reaction catalyst either supported or unsupported, as a solid, powder, or melt; generally the chloride of a multivalent metal, in particular, the chlorides of copper and iron, at a temperature from 450° F to 750° F to produce chlorinated hydrocarbons. The oxygen and hydrocarbon are mixed in proportions, as known in the art, to avoid explosive mixtures. The details of the oxychlorination of various hydrocarbons are well known in the art and, accordingly, no detailed description thereof is deemed necessary for a full understanding of the present invention. As representative examples of suitable oxychlorination reaction feeds, there may be mentioned both saturated and unsaturated aliphatic hydrocarbons, preferably $C_1$–$C_4$ aliphatic hydrocarbons; and aromatic hydrocarbons; in particular, benzene.

In accordance with the present invention, the ratio of hydrogen chloride to hydrocarbon is preferably controlled to provide essentially stoichiometric proportions of hydrogen chloride and hydrocarbon in order to avoid a loss of either hydrogen chloride and/or hydrocarbon in the vent gases; i.e., the ratio of hydrogen chloride to hydrocarbon is controlled to provide from about 5% below to about 10% above stoichiometric ratios. Although it is preferred to employ the present invention for maintaining about stoichiometric ratios of hydrogen chloride and hydrocarbon, it is to be understood that the present invention is not limited to such ratios in that the present invention can be employed to maintain other ratios of hydrogen chloride to hydrocarbon in an oxychlorination process.

The oxychlorination reaction effluent includes the chlorinated hydrocarbon, water vapor and hydrogen chloride, as well as non-condensibles, such as carbon oxides, and any nitrogen introduced with the oxygen. The aqueous hydrogen chloride can be recovered from the effluent by any one of a wide variety of procedures, with the aqueous hydrogen chloride preferably being recovered by cooling the gaseous effluent to effect condensation of the aqueous hydrogen chloride. The cooling may be effected either directly or indirectly, and in a preferred technique, the cooling may be effected to a temperature at which chlorinated hydrocarbon is also condensed from the oxychlorination reaction effluent. In general, cooling of the effluent to a temperature of from about 40° F to about 140° F. at a pressure in the order of from about 2 atm to 10 atm, will effect condensation of both aqueous hydrogen chloride and chlorinated hydrocarbon from the effluent.

The invention will be further described with respect to an embodiment thereof illustrated in the accompanying drawing wherein:

The drawing is a simplified schematic representation of an embodiment of the present invention.

Referring to the drawing, a hydrocarbon, such as ethylene, in line 10, hydrogen chloride in line 11 and air in line 12 are introduced into an oxychlorination reactor, schematically indicated as 13, wherein the ethylene is oxychlorinated to chlorinated hydrocarbons primarily, 1,2-dichloroethane. The oxychlorination is effected as known in the art.

An oxychlorination reaction effluent, including chlorinated hydrocarbon(s), in particular 1,2-dichloroethane, water vapor, non-condensible gas, in particular carbon oxides and nitrogen, and hydrogen chloride is withdrawn from zone 13 (generally at a temperature from 400° F to 500° F) through line 14 and passed through cooler 15 wherein the effluent is indirectly cooled to a temperature at which the major portion of the 1,2-dichloroethane is condensed from the effluent along with a dilute aqueous solution of hydrogen chloride. In general, the effluent is cooled in cooler 15 to a temperature in the order of from 40° F to 140° F.

The effluent withdrawn from cooler 15 in line 16 is introduced into a separator 17 wherein the condensate is separated from the remainder of the gaseous effluent. The remainder of the gaseous effluent is withdrawn from separator 17 through line 18 for further treatment.

The condensate, in separator 17, forms an organic phase, comprised of 1,2-dichloroethane which is withdrawn from separator 17 through line 19 for further treatment (not shown); for example, the 1.2-dichloroethane may be washed with caustic to remove chloral.

An aqueous phase, comprised of dilute hydrogen chloride, is withdrawn from separator 17 through line 21, and may be discarded. A conductivity controller 22, of a type known in the art senses the concentration of hydrogen chloride in the aqueous hydrogen chloride solution withdrawn through line 21. As hereinabove indicated, the concentration of hydrogen chloride in the aqueous solution in line 21 increases and decreases in response to increases and decreases, respectively, in the ratio of hydrogen chloride to ethylene introduced as feed into the oxychlorination reactor 13. Thus, if the ratio of hydrogen chloride to ethylene increases above a set desired value, the concentration of hydrogen chloride in the aqueous hydrogen chloride solution in line 21 will also increase to a value above a predetermined set value of hydrogen chloride concentration which corresponds to the set desired value of hydrogen chloride to ethylene feed ratio. In response to such an increase in the hydrogen chloride concentration in line 21, the conductivity controller operates to decrease the ratio of hydrogen chloride to ethylene introduced as feed in order to maintain the predetermined ratio. As particularly shown, the conductivity controller controls the amount of ethylene introduced into the reactor and, accordingly, in response to an increase in the hydrogen chloride concentration in line 21 above the preset value, the conductivity controller operates to increase the amount of ethylene introduced through line 10. It is to be understood that the conductivity controller could also be operated in a manner such as to control the amount of hydrogen chloride introduced into the oxychlorination reactor 13 through line 11, and in such a case, the conductivity controller would operate to decrease the amount of hydrogen chloride feed in response to an increase in the hydrogen chloride concentration in line 21.

Similarly, a decrease in the concentration of the hydrogen chloride in line 21 signifies a decrease from the predetermined hydrogen chloride to ethylene ratio and the conductivity controller would then operate to either decrease the ethylene feed, as shown, or in the case where the conductivity controller was operated to control the hydrogen chloride feed, the conductivity controller would operate to increase the hydrogen chloride feed.

The hydrogen chloride concentration which corresponds to the predetermined desired hydrogen chloride to ethylene feed ratio is predetermined in terms of the conductivity of the aqueous hydrogen chloride solution. An increase in the hydrogen chloride concentration in line 21, results in an increase in conductivity, and a decrease in the hydrogen chloride concentration results in a decrease in conductivity, and the amount of hydrogen chloride and/or ethylene feed is controlled in response to such increases and decreases in conductivity. It is also to be understood that the conductivity controller could be replaced by a density controller, which is responsive to the density of the aqueous hydrogen chloride solution withdrawn from separator 17 through line 21, with such increases and decreases in density being representative of changes in the hydrogen chloride concentration, which in turn is representative of changes in the hydrogen chloride to ethylene feed ratios.

The invention will be further described with respect to the following example.

EXAMPLE

In a plant where ethylene is oxychlorinated with HCl and excess air, the concentrations of the aqueous HCl solution produced for various ratios of HCl to ethylene are tabulated below.

| Ratio HCl/$C_2H_4$ | HCl In aqueous solution | Electrical Conductivity of Solution at 25° C |
|---|---|---|
| | wt % | mho/cm |
| 0.985 | 4.0 | 0.362 |
| 0.995 | 7.2 | 0.572 |
| 1.005 | 10.5 | 0.715 |

The accuracy of the conductivity meter is about 0.002 mho/cm. In the ratio range of 0.985 to 0.995 for HCl and ethylene the change of conductivity is 0.210. This means that a change of the ratio of 0.0001 can be detected. This is 0.01% of the change. In the ratio range of 0.995 to 1.005, the detectable change is 0.014%.

The accuracy of a conventional ratio meter is about 1%. Therefore, the present invention improves the accuracy of measurement 70-100 times.

The present invention is particularly advantageous in that the relative proportions of hydrogen chloride and hydrocarbon feed to an oxychlorination reaction can be maintained at a predetermined ratio by a simple measurement of conductivity and/or density of an aqueous hydrogen chloride stream recovered from the oxychlorination reaction effluent. The ability to closely control such feed ratios increases the ability to optimize yields.

Numerous modifications and variations of the present invention are possible in light of the above teachings and, therefore, within the scope of the appended claims, the invention may be practiced otherwise than as particularly described.

What is claimed is:

1. In a process for oxychlorinating a hydrocarbon by direct contact of a hydrocarbon, oxygen and hydrogen chloride feed to produce a gaseous effluent, containing chlorinated hydrocarbon, water vapor and hydrogen chloride, the improvement comprising:

recovering aqueous hydrogen chloride from said gaseous effluent;

determining the hydrogen chloride concentration of said recovered aqueous hydrogen chloride; and controlling at least one of the hydrogen chloride and hydrocarbon feeds to increase and decrease the proportion of hydrogen chloride to hydrocarbon in response to changes in the hydrogen chloride concentration of said recovered aqueous hydrogen chloride from a predetermined hydrogen chloride concentration to thereby maintain said predetermined hydrogen chloride concentration which corresponds to a predetermined desired hydrogen chloride to hydrocarbon feed ratio.

2. The process of claim 1 where in the hydrogen chloride to hydrocarbon feed ratio is maintained at a value of from about 5% below to about 10% above the stoichiometric hydrogen chloride to hydrocarbon feed ratio.

3. The process of claim 2 wherein the hydrocarbon is ethylene.

4. The process of claim 1 wherein the hydrogen chloride concentration of the recovered aqueous hydrogen chloride is determined by measuring the conductivity of the recovered aqueous hydrogen chloride.

5. The process of claim 4 wherein the hydrogen chloride to hydrocarbon feed ratio if maintained at a value of from about 5% below to about 10% above the stoichiometric hydrogen chloride to hydrocarbon feed ratio.

6. The process of claim 5 wherein the hydrocarbon is ethylene.

7. The process of claim 6 wherein the aqueous hydrogen chloride is recovered by cooling the effluent to effect condensation of aqueous hydrogen chloride.

* * * * *